US00PP14745P3

(12) United States Plant Patent
Moser

(10) Patent No.: US PP14,745 P3
(45) Date of Patent: May 4, 2004

(54) CHRYSANTHEMUM PLANT NAMED 'MOZA CON 02'

(50) Latin Name: *Chrysanthemum morifolium*
Varietal Denomination: Moza Con 02

(75) Inventor: Frank Moser, Alva, FL (US)

(73) Assignee: Mozant, LLC, Oxnard, CA (US)

( * ) Notice: Subject to any disclaimer, the term of this patent is extended or adjusted under 35 U.S.C. 154(b) by 0 days.

(21) Appl. No.: 10/136,685

(22) Filed: Apr. 30, 2002

(65) Prior Publication Data

US 2003/0204889 P1 Oct. 30, 2003

(51) Int. Cl.[7] ..... A01H 5/00
(52) U.S. Cl. ..... Plt./287

(58) Field of Search ..... Plt./287

(56) References Cited

U.S. PATENT DOCUMENTS

PP10,064 P 10/1997 Hammett ..... Plt./741

*Primary Examiner*—Bruce R. Campell
*Assistant Examiner*—Annette H Para
(74) *Attorney, Agent, or Firm*—Knobbe, Martens, Olson & Bear, LLP

(57) ABSTRACT

A new and distinct Chrysanthemum plant cultivar is disclosed, characterized by a decorative-type inflorescence, consistent flowering response to short days, blooming consistently after 49 days of short day length, free branching habit, light pink ray florets, a very uniform round growth habit, and a large quantity of blooms per flowering branch.

1 Drawing Sheet

Latin name of the genus and species: The present invention relates to a new and distinct cultivar of Chrysanthemum plant, botanically known as *Chrysanthemum morifolium.*

Variety denomination: The new and distinct Chrysanthemum plant is hereinafter referred to by the cultivar name 'Moza Con 02.'

BACKGROUND OF THE INVENTION

The new cultivar is a product of hybridization of a female parent Chrysanthemum plant variety 'MZ-195' (undistributed in the United States) and a male parent Chrysanthemum plant variety 'MZ-28' (undistributed in the United States). The new cultivar was discovered and selected by the inventor in October 1999.

Asexual reproduction of the new cultivar by apical tip cutting and meristem tissue culture was performed in Oxnard, Calif. and has shown that the unique features of this cultivar are stable and reproduced true to type on successive generations.

SUMMARY OF THE INVENTION

The cultivar 'Moza Con 02' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Moza Con 02.' These characteristics in combination distinguish 'Moza Con 02' as a new and distinct Chrysanthemum cultivar:

1. Decorative-type inflorescence,
2. Consistent flowering response to short days, blooming consistently after 49 days of short day length,
3. Free branching habit, 4. Light pink ray florets,
5. Very uniform round growth habit, and
6. Large quantity of blooms per flowering branch.

Plants of the new cultivar are similar to plants of the female parent variety, 'MZ-195' in most horticultural characteristics, however plants of the new cultivar have a different inflorescence form and differently colored ray florets than plants of the female parent variety.

Plants of the new cultivar are similar to plants of the male parent variety, 'MZ-28' in most horticultural characteristics, however plants of the new cultivar have a different inflorescence form and differently colored ray florets than plants of the male parent variety.

In comparison to the commercially available variety 'Flirtation' (U.S. Plant Pat. No. 10,064), 'Moza Con 02' has a smaller diameter inflorescence, many more ray florets per inflorescence, a different inflorescence type, and more inflorescences per flowering branch.

BRIEF DESCRIPTION OF THE PHOTOGRAPH

The photograph shows a plant of 'Moza Con 02' grown in a six-inch container. One cutting was used in the pot.

DETAILED BOTANICAL DESCRIPTION

In the following description, color references are made to The Royal Horticultural Society Colour Chart except where general terms of ordinary dictionary significance are used. The following observations and measurements describe 82 day old plants grown in Oxnard, Calif. during the month of December and January. The growing temperature ranged from 55° to 68° F. at night to 60° to 75° F. during the day. Measurements and numerical values represent averages of typical flowering types.

Botanical classification: *Chrysanthemum morifolium* cultivar 'Moza Con 02'.

Commercial classification: Garden-type Chrysanthemum.
Parentage: Hybridization of a female parent Chrysanthemum plant variety, 'MZ-195' (undistributed in the United States), and a male parent Chrysanthemum plant variety 'MZ-28' (undistributed in the United States).

PROPAGATION

Time to rooting: 7 to 14 days at approximately 21° C.
Rooting habit: Fine, fibrous.

PLANT

Growth habit: Mounding herbaceous perennial.
Height: Approximately 17.3 cm.
Spread: Approximately 18.5 cm.
Growth rate: Moderate.
Branching characteristics: Free Branching.
Length of lateral branches: Approximately 14.8 cm.
Number of leaves per lateral branch: Approximately 27.

FOLIAGE

Leaf:
- *Arrangement.*—Alternate.
- *Average length.*—Approximately 4.7 cm.
- *Average width.*—Approximately 4 cm.
- *Shape of blade.*—Ovate.
- *Apex.*—Cuspidate.
- *Base.*—Attenuate.
- *Attachment.*—Stalked.
- *Margin.*—Palmately lobed.
- *Texture of top surface.*—Lightly pubescent.
- *Texture of bottom surface.*—Lightly pubescent.
- *Color.*—Young foliage upper side: Near 137B. Young foliage under side: Near 138B. Mature foliage upper side: Near 137A. Mature foliage under side: Near 138B. Venation upper side: Near 145B. Venation under side: Near 138C.
- *Type.*—Net.

Petiole:
- *Average length.*—Approximately 1.7 cm.
- *Color.*—Near 137A.
- *Diameter.*—Approximately 0.3 cm.

BLOOM

Inflorescence:
- *Flowering habit.*—Induced by darkness period greater than 13.5 hours, approximately 49 days of appropriate day length required to induce and develop blooms.
- *Inflorescence form.*—Decorative.
- *Natural flowering season.*—Approximately the first two weeks of September.
- *Number of inflorescences per lateral branch.*—Approximately 14.
- *Inflorescence diameter.*—Approximately 2.5 cm.
- *Inflorescence depth.*—Approximately 1.3 cm.
- *Inflorescence longevity on plant.*—Approximately 24 days.
- *Persistence.*—Persistent.
- *Changes with aging.*—Ray floret color fades and disc florets may begin to show.

Ray florets:
- *Appearance.*—Matte.
- *Texture.*—Smooth.
- *Average number per flower.*—93.
- *Shape.*—Obovate.
- *Aspect.*—Flat.
- *Margin.*—Entire.
- *Apex.*—Obcordate.
- *Length.*—Approximately 1 cm.
- *Width.*—Approximately 0.5 cm.
- *Color.*—Upper surface at first opening: Near 69C at base and gradually darkening to near 75B at tip. Upper surface at maturity: Near 69D at base and gradually darkening to near 75C at tip. Upper surface at fading: Near 69D. Under surface at first opening: Near 69C at base and gradually darkening to near 75A at tip. Under surface at maturity: Near 155D at base and gradually darkening to near 75C at tip. Under surface at fading: Near 155D at base and gradually darkening to near 75D at tip.

Disc florets:
- *Appearance.*—Shiny.
- *Texture.*—Smooth.
- *Average number per flower.*—Approximately 3.
- *Shape.*—Cylindrical.
- *Apex.*—Obtuse.
- *Average length.*—Approximately 0.4 cm.
- *Average width.*—Approximately 0.1 cm.
- *Color.*—At first opening: Near 14B. At maturity: Near 13A. At fading: Near 13A.

Peduncle:
- *Length.*—At terminal end (shortest): Approximately 4.2 cm. At lateral end (longest): Approximately 6 cm.
- *Angle to stem.*—Acute.
- *Strength.*—Moderate.
- *Color.*—Near 143C.
- *Habit.*—Upright.
- *Diameter.*—Approximately 0.2 cm.
- *Texture.*—Pubescent.
- *Internode length.*—Approximately 2.2 cm.

Inflorescence bud:
- *Length.*—Approximately 0.5 cm.
- *Diameter.*—Approximately 0.7 cm.
- *Form.*—Globular.
- *Color.*—Near 69C.

Involucral bracts (phyllaries):
- *Appearance.*—Matte.
- *Texture.*—Lightly pubescent.
- *Number.*—Approximately 29.
- *Shape.*—Oblanceolate.
- *Margin.*—Entire.
- *Apex.*—Acute.
- *Length.*—Approximately 0.7 cm.
- *Width.*—Approximately 0.3 cm.
- *Color.*—Upper side: Near 143A. Under side: Near 143A.

REPRODUCTIVE ORGANS

Ray florets:
- *Pistillate.*—Number of pistils per flower: 1. Stigma shape: 2 branched. Stigma color: Near 9A. Style color: Near 154C. Style length: Approximately 0.5 cm.

Disc florets (hermaphroditic):
- *Pistillate.*—Number of pistils per flower: 1. Stigma shape: Two-branched. Stigma color: Near 9A. Style length: Approximately 0.5 cm. Style color: Near 154C.
- *Staminate.*—Number of stamens per flower: 5. Anther shape: Tubular. Anther color: Near 13A. Pollen color: Near 13A.

OTHER CHARACTERISTICS

Seed production: Commercially, this plant is not used or observed in a stage wherein seeds would be produced. Therefore, seed production has not been observed.

Disease resistance: Neither resistance nor susceptibility has been observed.

Cold tolerance: Flowering plants are resistant to cold to approximately 0° C. Non-flowering plants have been observed to withstand cold temperatures to approximately −4° C.

Drought tolerance: Plants will come back with little damage from a full wilt. Plants usually will not tolerate prolonged drought (over 7 days without any water).

What is claimed is:

1. A new and distinct cultivar of Chrysanthemum plant named 'Moza Con 02' as herein illustrated and described.

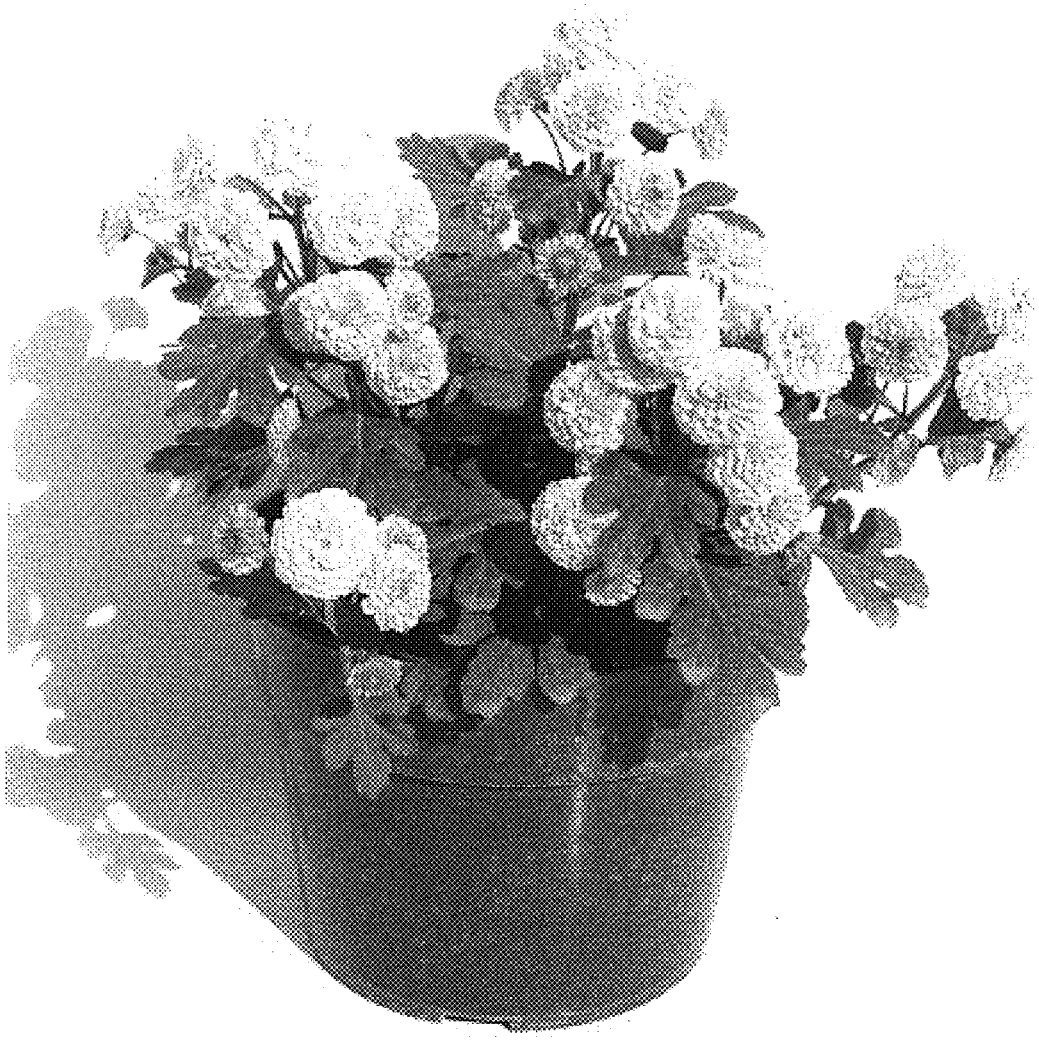

* * * * *